United States Patent [19]
Gonser et al.

[11] Patent Number: 5,045,055
[45] Date of Patent: Sep. 3, 1991

[54] FLOW CONTROL VALVE ASSEMBLY FOR SYRINGES

[75] Inventors: Donald I. Gonser; Douglas M. Reinhart, both of Lancaster, Pa.

[73] Assignee: Den-Tal-Ez, Inc., Audubon, Pa.

[21] Appl. No.: 535,040

[22] Filed: Jun. 7, 1990

Related U.S. Application Data

[62] Division of Ser. No. 260,932, Oct. 21, 1988, Pat. No. 4,957,483.

[51] Int. Cl.⁵ .............................................. A61G 17/02
[52] U.S. Cl. ..................... 604/33; 604/249; 433/80; 137/454.2; 251/322
[58] Field of Search ................. 604/33, 246, 249, 275; 433/80, 99, 100; 137/454.2; 251/322, 321

[56] References Cited

U.S. PATENT DOCUMENTS

| | | | |
|---|---|---|---|
| 3,500,824 | 3/1970 | Gilbert . | |
| 3,593,423 | 7/1971 | Jones | 433/80 |
| 3,640,304 | 2/1972 | Fox et al. | 433/80 |
| 3,698,088 | 10/1972 | Austin, Jr. . | |
| 3,874,083 | 4/1975 | Buckley | 433/80 |
| 4,047,527 | 9/1977 | Kelsen | 604/249 |
| 4,111,392 | 9/1978 | Edelmann | 251/322 |
| 4,149,315 | 4/1979 | Page, Jr. et al. . | |
| 4,729,543 | 3/1988 | Aricha | 137/454.2 |
| 4,957,483 | 9/1990 | Gonser et al. | 433/80 |

Primary Examiner—Stephen C. Pellegrino
Assistant Examiner—Ralph A. Lewis
Attorney, Agent, or Firm—Howson and Howson

[57] ABSTRACT

A sterilizable medical/dental syringe having a handle with a nozzle at one end is provided with means for releasably coupling the other end of the handle to a flexible supply hose providing compressible gases and-/or noncompressible liquids. When disconnected from the flexible hose supply line, automatic sealing valves prevent the contents of the supply line from escaping. A readily repairable flow control valve for the nozzle is also disclosed.

5 Claims, 4 Drawing Sheets

FLOW CONTROL VALVE ASSEMBLY FOR SYRINGES

CROSS-REFERENCE TO RELATED APPLICATION

The present application is a division of copending application Ser. No. 07/260,932, filed on Oct. 21, 1988 and entitled STERILIZABLE SYRINGE, now U.S. Pat. No. 4,957,483.

BACKGROUND OF THE INVENTION

The present invention relates to syringes, and more particularly, the present invention relates to medical/dental syringes capable of being sterilized readily.

Syringes for use by medical and dental personnel to flow water or air into a body cavity, such as the oral cavity, have been known for quite some time. A typical syringe includes a handle having a proximal end with a nozzle and one or more finger actuated valves for controlling flow through the nozzle. The handle has a distal end which is connected to at least one, and preferably two or more flexible hoses each of which is connected to a source of fluid under pressure. For instance, one hose may be connected to air under a line pressure of 80 psig, and the other hose may be connected to water under a pressure of 45 psig. The flow control valves, when actuated, cause either water or air, or a mixture of water and air to be discharged from the nozzle into the body cavity. An example of a desirable syringe having the aforementioned structural and functional features is disclosed in U.S. Pat. No. 4,149,315.

In the aforementioned patent, and in U.S. Pat. Nos. 2,029,734; 3,254,646; and 4,026,025 the nozzles are detachably secured to the proximal ends of the handles which enable the nozzles to be sterilized periodically. In each of these patented syringes, however, the distal ends of the handles are secured to end portions of the flexible hoses in essentially a permanent manner. As a result, although the nozzles can be removed for sterilization, the handles, being connected to the hoses, are not readily capable of being sterilized by effective sterilization techniques, such as by placement in an autoclave. Thus, while the aforementioned syringes having removable nozzles provide some measure of sterilizability, it would be more desirable for the entire syringe to be capable of being sterilized after each use in order to provide as much protection as possible against the transmission of disease.

OBJECTS OF THE INVENTION

An object of the present invention is to provide an improved syringe which is capable of being sterilized in an autoclave, chemiclave, dry clave, or other method of sterilization and which has replaceable components that resist deterioration due to high temperature or chemical action during sterilization.

SUMMARY OF THE INVENTION

More specifically, in the present invention, a syringe having a handle with a proximal end portion and a nozzle, a flow control valve for the nozzle, and a distal end is provided with coupling means for releasably connecting the distal end to a flexible hose connected to a source of fluid. The coupling means includes a first coupling component adapted to be mounted on the hose and a second coupling component carried by the distal end portion of the handle. The first and second coupling components ar telescopically matingly engageable and disengageable with one another and have cooperating valving and actuator means which operate automatically upon engagement to provide fluid communication between the hose and the handle when the coupling components are interconnected and to block fluid communication when disconnected. The flow control valve for the nozzle is specially designed to withstand high temperature sterilization, to provide excellent chemical resistance, and to be capable of readily being disassembled and reassembled in the field.

BRIEF DESCRIPTION OF THE DRAWINGS

The foregoing and other objects, features and advantages of the present invention should become apparent from the following description when taken in conjunction with the accompanying drawings, in which.

DESCRIPTION OF THE PREFERRED EMBODIMENTS

Figure 1:
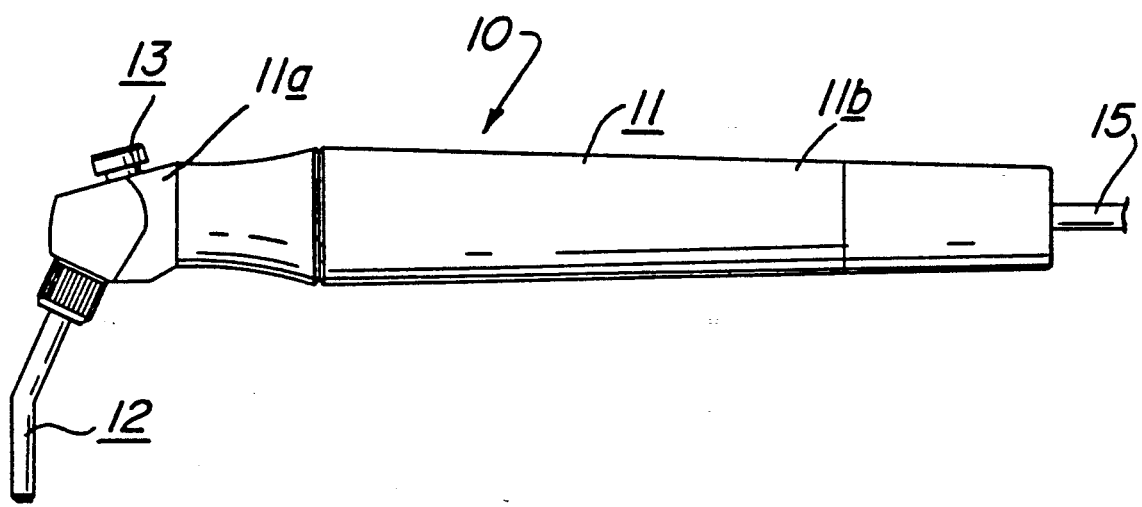
FIG. 1 is a side elevational view of a sterilizable syringe embodying the present invention.

Referring now to the drawings, FIG. 1 illustrates a syringe 10 which embodies the present invention. Outwardly, the syringe 10 is similar in appearance to the syringe illustrated in U.S. Pat. No. 4,149,315, the disclosure of which is incorporated by reference herein. As described in that patent, which is owned by the assignee of this application, the syringe 10 is particularly suited for use in medical and dental applications where it is desired to flow either a fluid, such as water, or a gas such as air, into a body cavity, such as an oral cavity in a dental operatory. As used herein, fluid is defined as either a compressible gas or noncompressible liquid.

Figure 2:
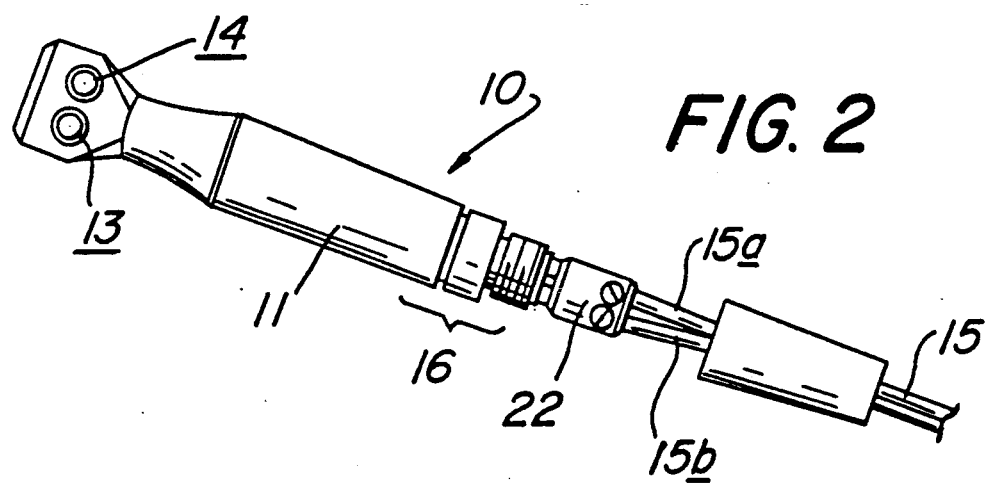
FIG. 2 is a plan view of the syringe illustrated in FIG. 1, but with a portion partially disassembled to expose interior details of construction.

The syringe 10 comprises an elongate handle 11 having a proximal end portion 11a to which is secured a nozzle 12 from which a fluid may be flowed, such as in the manner described in the aformentioned patent. The proximal end, or valve body head, 11a of the handle 11 also has one or more push button control valves having finger actuators, such as the actuators 13 and 14 shown in FIG. 2. The handle 11 has a distal end portion 11b connected to a flexible hose assembly 15. As shown in FIG. 2, the hose assembly 15 includes a tube 15a connected to a source of water (not shown) and a tube 15b connected to a source of air (not shown). By selective operation of the valve actuators 13 and 14, either water, or air, or a mist can be discharged from the nozzle 12 into a body cavity.

As discussed herefore, one of the problems associated with syringes of conventional design is that they are not capable readily of being connected to and disconnected from the air and water supply hose assembly 15. Thus, even though some may have nozzles that can be disconnected for sterilization, the handle portions usually remain firmly connected to the hose assembly. Thus, they are difficult to sterilize effectively.

The present invention overcomes the aforementioned drawbacks associated with conventional syringes by providing a syringe which can be quickly connected to and disconnected from a flexible hose assembly without requiring any special tools. This enables the entire syringe to be removed from the dental or medical operatory for sterilization in an autoclave. As a result, the syringe, and particularly the proximal end portions thereof which are normally placed in close proximity with a body cavity, can be sterilized readily and effectively.

Figure 4:
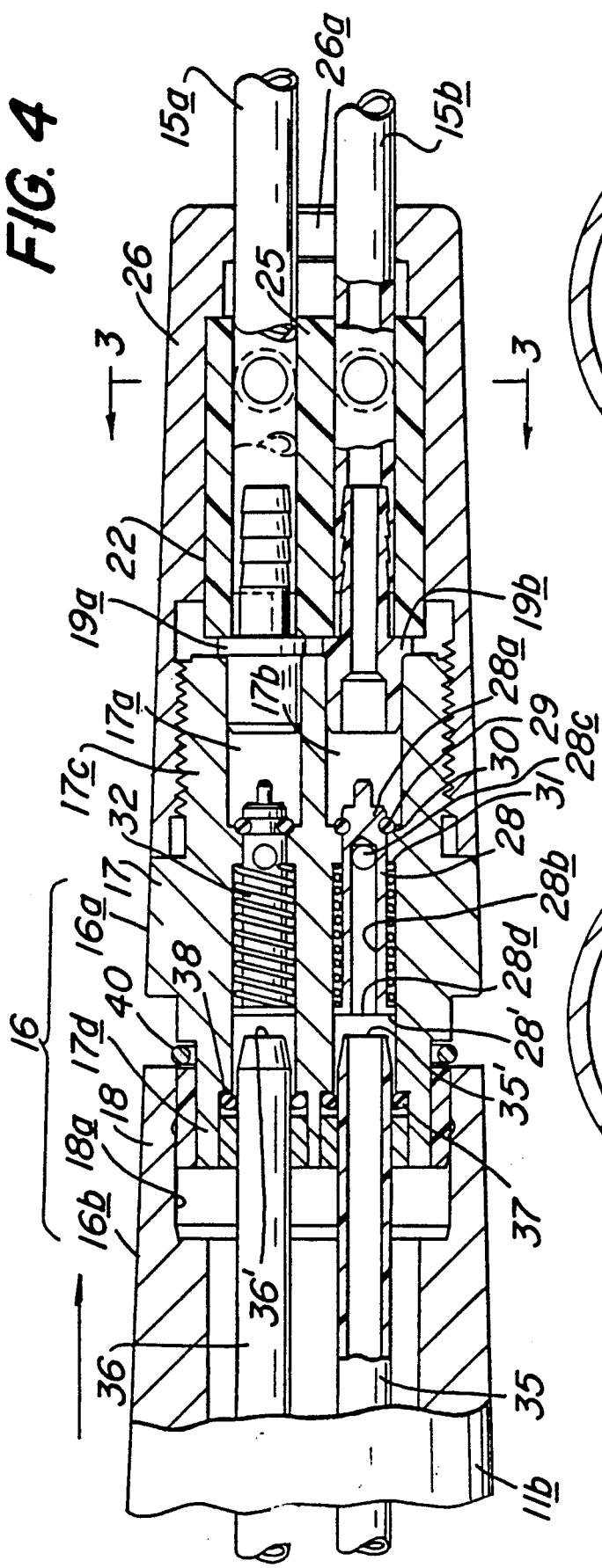
FIG. 4 is an enlarged longitudinal sectional view of the distal end portion of the syringe illustrated in FIG. 1, but showing the various components immediately prior to coupling.

To this end, a means 16 (FIG. 2) is provided for releasably coupling the distal end portion 11b of the handle 11 to the hose assembly 15. In the illustrated embodiment, (FIG. 4) this is accomplished by first and second coupling components 16a, 16b which are telescopically matingly engageable and disengageable with one another and which have cooperating valving and actuator means operable automatically upon engagement to provide fluid communication between the hose assembly 15 and the handle 11 when interconnected and to block fluid communication when disconnected. The first and second coupling components providing the coupling means 16 are indicated generally within the region denominated by the reference numeral 16 in FIG. 2. As best seen in FIG. 4 (Sheet 2) the coupling means 16 includes a first coupling component 16a carried on the end portions of the hoses 15a, 15b and a second coupling component 16b carried on the distal end portion 11b of the syringe handle 11. The first coupling component 16a is provided by a cylindrical body 17 having a pair of valve chambers 17a, 17b each of which telescopically receives a union, such as the unions 19a and 19b, respectively. The unions 19a and 19b have barbed portions, engaged inside the end portions of the hoses 15a and 15b.

Figure 3:
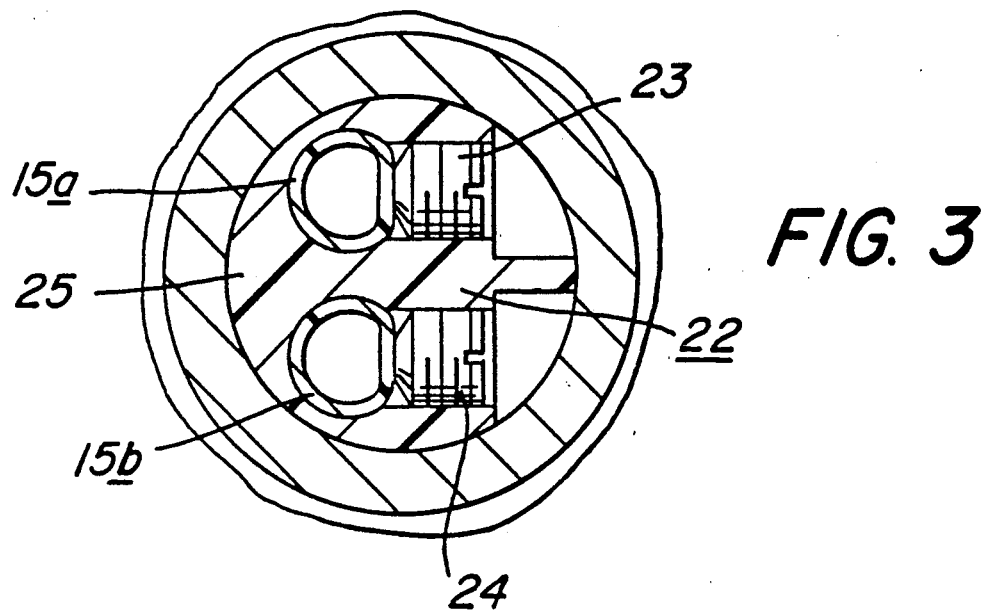
FIG. 3 is a transverse sectional view taken on line 3—3 of FIG. 4.

For enabling flow rate adjustments to be made, a pinch valve assembly 22 is provided on the upstream side of the coupling body 17. As best seen in FIG. 4, the pinch valve assembly 22 includes a valve block 25 having a pair of through bores which receive the hose end portions 15a, 15b and the unions 19a and 19b in the manner illustrated. As best seen in FIG. 3, the pinch valve assembly 22 includes a pair of set screws 23 and 24 threaded into the pinch valve block 25. The set screws 23 and 24 are operable, when rotated in one direction or another in a well-known manner, to compress the walls of the hoses 15a, 15b to restrict the flow of air or water therethrough.

To mount the pinch valve assembly 22, the coupling component body 17 has an externally threaded portion 17c which rotatably receives a complementary threaded portion of a tubular ferrule 26. The ferrule 26 has an open end 26a rotatably receiving the hose end portions 15a, 15b. Thus, when engaged in the manner illustrated in FIG. 4, the ferrule 26 secures the pinch valve block assembly 22 in position at the right, or upstream, end of the coupling body 17 for causing either air and water under pressure to be supplied continuously to the valve chambers 17a and 17b, respectively at a preselected flow rate.

Figure 5:
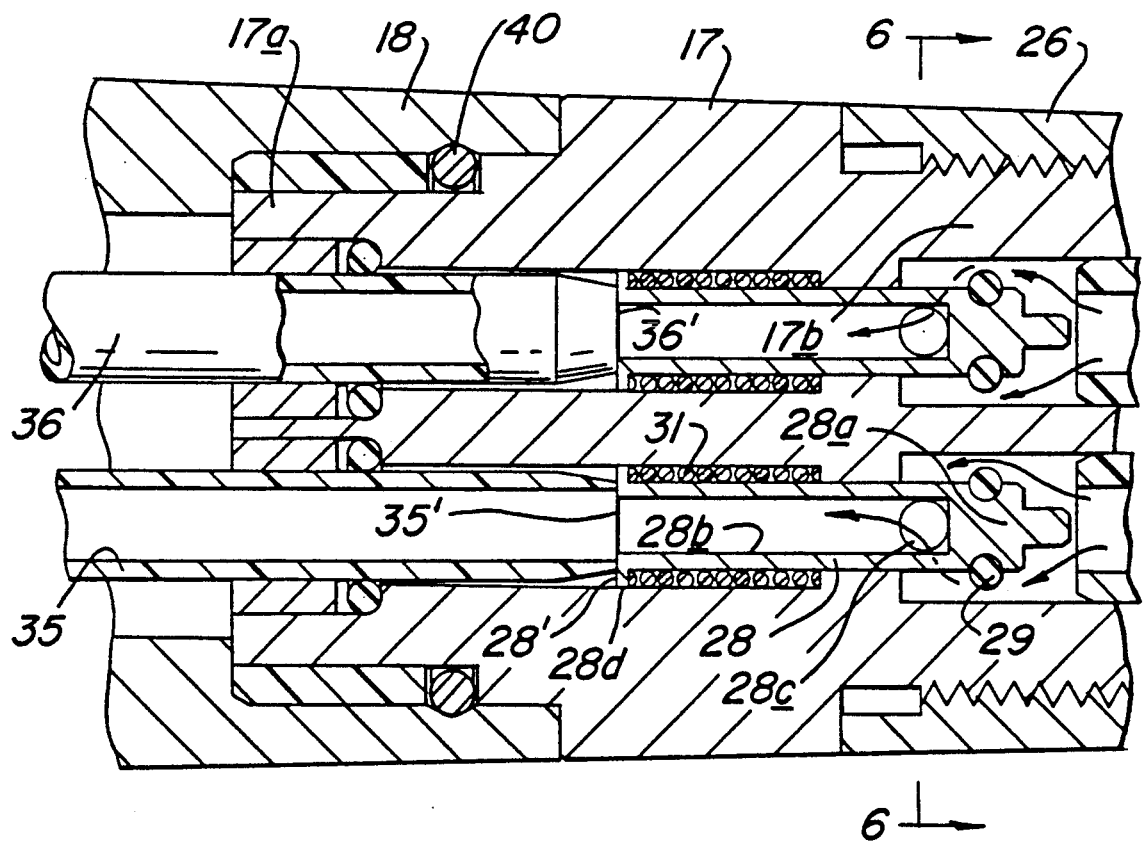
FIG. 5 is an enlarged fragmentary cross-sectional view of a portion of the assembly illustrated in FIG. 4 but illustrating the components in operative engagement providing fluid communication between the hose and syringe.
Figure 6:
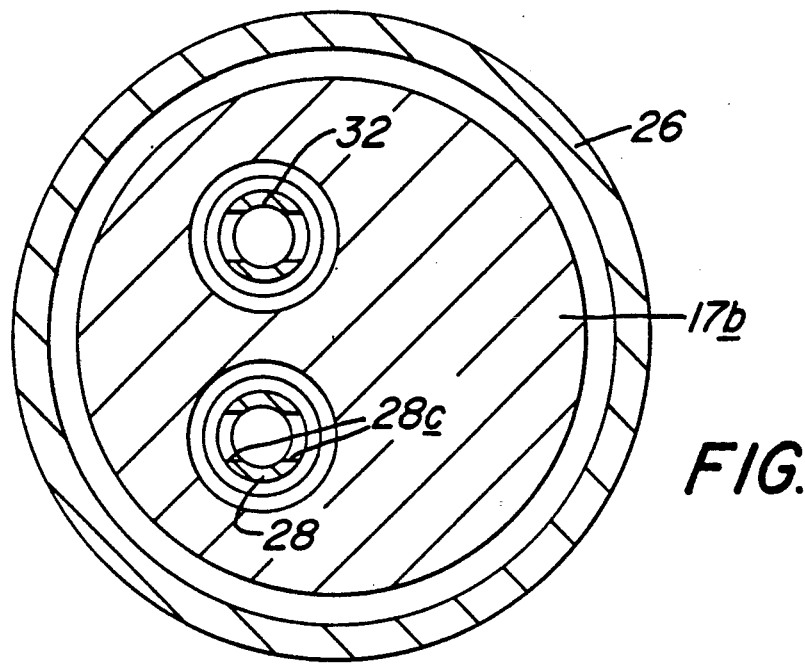
FIG. 6 is a transverse sectional view taken on line 6—6 of FIG. 5.

In order to block fluid flow from the valve chambers 17a and 17b when the coupling components 16a and 16b are disconnected, each valve chamber is provided with a valve member movable between a seated position illustrated in FIG. 4 and an unseated position illustrated in FIG. 5. Each valve member, such as the valve member 28 associated with the chamber 17b, has a head 28a mounting an 0-ring 29 adapted to engage a seat 30 confronting the valve chamber 17b. In the illustrated embodiment, the valve member 28 is preferably of hollow tubular form having a central passage 28b which communicates adjacent its head 28a with a pair of lateral ports 28c (FIG. 6). The valve member 28 has a peripheral flange 28' opposite its head end 28a around an axial end port 28d. A helical compression spring 31 is engaged between the flange 28' and a shoulder in a bore slidably receiving the valve member 28 to bias the valve member 28 into its closed position illustrated in FIG. 4. In such position, the lateral ports 28c are sealed from the valve chamber 17b by the engagement of the 0-ring 29 with its seat 30. The valve member 32 associated with the other chamber 17a is of like construction and operates in the same manner as the valve 28. Thus, both valves 28 and 32 are maintained in a normally flow blocking relation with respect to their respective chambers to prevent fluid under pressure from being discharged from the chambers 17a and 17b until actuated.

For the purpose of unseating the valves 28 and 32 and of providing fluid communication between the valve chambers 17b and 17a, respectively and the syringe nozzle 12, actuator means is provided in the second coupling component 16b on the handle 11. In the illustrated embodiment, as best seen in FIG. 4, the actuator means includes a pair of conduits 35 and 36 extending in spaced parallel relation axially inside the handle 11 from its proximal end portion 11a to its distal end portion 11b. In the present instance, the second coupling component 16b is provided by a tubular extension wall 18 which is located on the distal end 11b of the handle 11 and which surrounds the end portions of the conduits 35 and 36 and provides a recess 18a in the distal end 11b of the handle 11. The coupling component body 17 has a boss 17d which is sized to be telescopically received within the recess 18a. When initially arranged in the manner illustrated in FIG. 4, the passages in the conduits 35 and 36 are aligned axially with the passages in the valves 28 and 32, but when pushed together into the position illustrated in FIG. 5, the ends 35', 36' of the conduits 35, 36, respectively, engage the open ends of valves 28 and 32, respectively and displace the valves 28 and 32 rightward into their fully open positions. To prevent leakage when the valves are thus opened, 0-rings 37 and 38 are mounted in grooves in the coupling component body 17 and surround the outer peripheries of the conduits 35 and 36. The ends of the conduits 35 and 36 are tapered as illustrated to facilitate insertion.

To provide a desirable snap-together releasable connection, a split circular spring ring 40 is mounted in a groove on the downstream end 17d of the coupling component body 17, and the spring ring 40 is adapted to engage in an interior groove 18b in the other coupling component wall 18 in the manner illustrated in FIG. 5 when the coupling components 16a and 16b are matingly telescopically engaged with one another. Preferably, the spring ring 40 and its complementary groove 18b are designed to provide a snap-together connection which keeps the components connected under fluid pressures as high as 80 psig, but permits disconnection at an axial force of at least 8 lbs., but less than about 16 lbs.

When the coupling components 16a and 16b are matingly engaged, the valves and valve actuators are in the positions illustrated in FIG. 5. In such position, both the valve members 28 and 32 are displaced rightward by the engagement therewith of the ends of the conduits 35 and 36 which function as valve actuators. In the riqhtwardmost displaced position, fluid flows from the valve cavities 17a, 17b, into the lateral ports of the valve members 28 and 32 and axially through the valve members into the tubes 35, 36 to the proximal end 11a of the handle 1 for discharge from the nozzle 12 by selective actuation of the valve actuators 13, 14. When it is desired to sterilize the syringe 10, the handle 11 is simply pulled axially and its coupling component 16b disconnected from the coupling component 16a on the hose assembly 15. When pulled apart, the conduits 35 and 36 are disengaged completely from the ends of the valves 32 and 28 respectively, enabling the valve springs to return the valves to their closed positions illustrated in FIG. 4 to prevent leakage of the noncompressable liquid and compressable gas from the valve chambers 17a and 17b. The thus removed syringe 10 can be sterilized by conventional techniques, such as the application of high temperature heat in an autoclave, chemiclave, or dry heat sterilizer.

Figure 7:
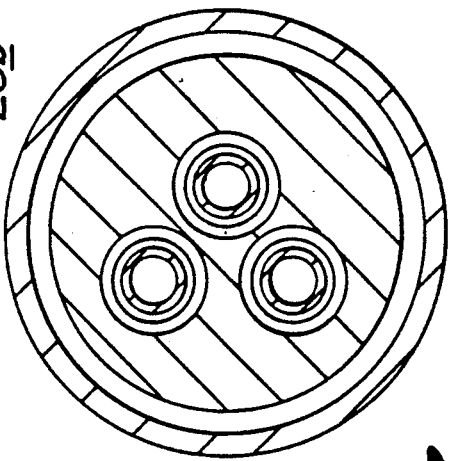
FIG. 7 is a transverse sectional view, similar to FIG. 6, but of a modified embodiment of the present invention.

In the embodiment of FIGS. 1-6, air and water are supplied to the nozzle via the two valved flow paths illustrated. If desired, however, warm water may be continually supplied to the proximal end of the syringe by flowing it forwardly through one conduit to the valve body head 11a of FIG. 1 through a Tee connection and returning any unused portion rearwardly through a third exit conduit in the handle to maintain continuity of flow, and hence constant delivery temperature. In such event, three conduits and complementary valve assemblies may be provided and arranged such as in the manner illustrated in cross section in FIG. 7. In this embodiment, two valve actuators are provided, one for air the other for warm water input and the third for the exit of return water.

Figure 8:
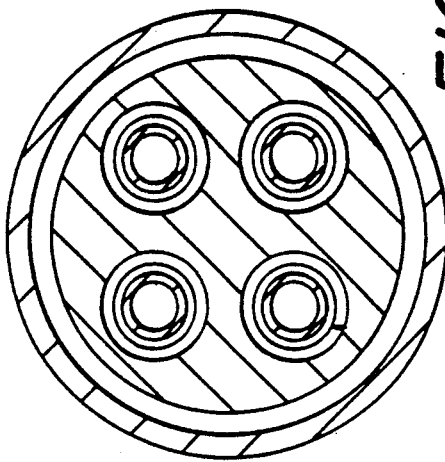
FIG. 8 is a transverse sectional view, similar to FIG. 7, but illustrating a further modified embodiment of the present invention.

If desired, a plurality of conduits for various purposes may be provided in the handle of the syringe with each being provided with its own flow control valve. For instance, one of the conduits may be used to supply air to the nozzle, another to supply either warm or cool water, and a third to supply a liquid medicament. A fourth conduit may be provided and utilized either as a return for warm water, or possibly, to provide a mouth wash deliverable from the nozzle. Still another combination for use in dentistry is to provide compressed air, pressurized water, a local topical anesthetic, and a mouth wash. In medical applications, for example, in cleaning and preparing infected wounds, such as the treatment of decubitus skin ulcers, a source of nitrogen gas, sterile and distilled water, a debridement agent, such as, hydrogen peroxide, and medicament are used. Such combination can be provided on a mobile cart delivery system with the supply of all four fluids contained in pressurized canisters which will permit convenient bedside use in a hospital setting. The advantage of syringe delivery is that this method minimizes the potential of wound recontamination during the debridement and treatment procedure. These four conduits may be arranged as illustrated in cross-section in FIG. 8.

In the illustrated embodiment, the snap-together type connection is provided by a split circular spring ring carried on one component and an interior complementary mating groove in the other. If desired, however, other means may be provided which afford rapid connection and disconnection without the use of tools. For instance, ball detent mechanisms, bayonet-type connections, 0-ring type mechanisms and high pitch treads may be used, as desired. In the disclosed embodiment, the 0-rings are of a material that resists repeated subjection to high temperatures, such as the 600° F. temperature in a sterilization process. The preferred material is a fluorocarbon manufactured under the trade designation VITON. Various other parts of the syringe are preferably fabricated of plated brass, stainless steel and/or hard anodized aluminum.

Over a prolonged period of time, repeated subjection of the syringe to the high temperatures associated with autoclave or other sterilization methods may cause the 0-ring associated with the flow control valves 13 and 14 to lose their effectiveness. In order to overcome this difficulty, the flow control valves 13 and 14 have been designed to enable their 0-rings to be removed readily in the field and replaced periodically. To this end, the embodiment of FIG. 9 is provided.

Figure 9:
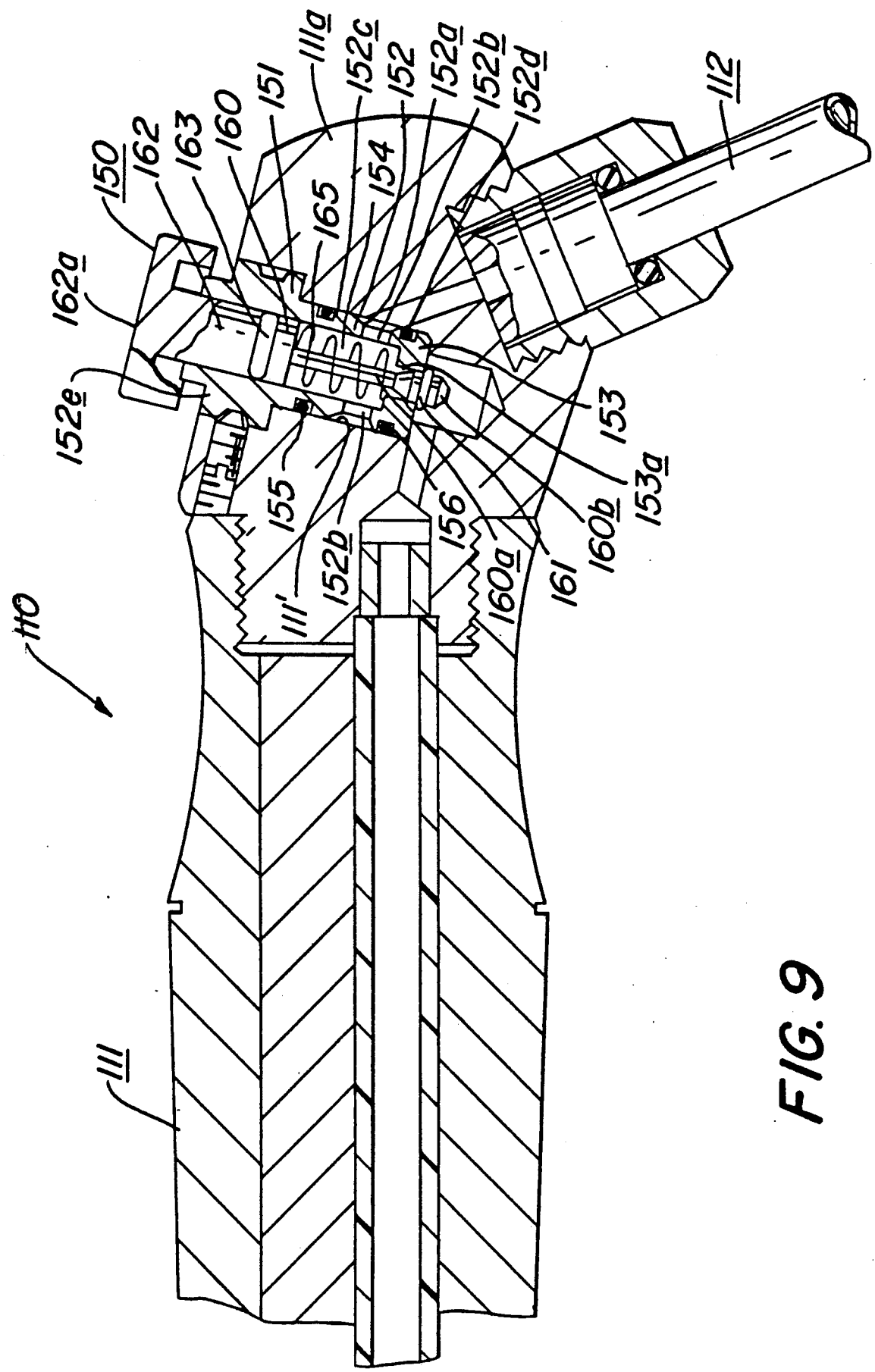
FIG. 9 is an enlarged fragmentary longitudinal sectional view of a flow control valve according to the present invention.

Except for the novel construction of the flow control valves, to be described, and the coupling means described heretofore, the syringe 110 illustrated in FIG. 9 is otherwise structurally the same as that illustrated in FIGS. 1 and 4 of U.S. Pat. No. 4,149,315, the disclosure of which is incorporated by reference herein. The flow control valve illustrated in FIG. 5 of that patent is fabricated of a series of components which are assembled in a manner which prevents them from being disassembled in the field. As a result, the flow control valve in the patented structure must be removed, discarded and replaced when worn. Not only is this economically undesirable, but the flow control valve structure itself is not inexpensive to manufacture.

Therefore, according to another aspect of the present invention, a flow-control valve is provided which can be manufactured economically and removed easily in the field for replacement of 0-rings, and while it is particularly suited for the autoclavable syringe illustrated in FIGS. 1-8, it may also be used in a syringe such a described in the aforementioned patent.

Referring now to FIG. 9, a syringe 110 having a handle 111 with a proximal end portion 111a and a nozzle 112 is provided with a flow control valve assembly 150 of the present invention.

The flow control valve assembly 150 is mounted in a recess provided by a circular wall 111' in the proximal end 111a of the syringe 111 for controlling fluid flow between the conduits in the handle 111 and the nozzle 112 in the same manner as described in the aforementioned patent. In the present invention, however, the valve assembly 150 includes a one-piece valve body 151 having a tubular side wall 152 and an end wall 153. The tubular side wall 152 has an outer peripheral groove 152a and one or more ports 152b opening into a central cavity 154. The end wall 153 has an axial port 153a which also communicates with the cavity 154. A pair of axially spaced grooves 152c and 152d are provided on opposite sides of the ports 152b and mount 0-rings 155 and 156, respectively for sealingly engaging the syringe wall 111'. The upper end of the valve body side wall 152 is provided with an annular flange 152e having a groove 152f which is engageable by a set screw 157 for removably mounting the valve body 151 in place.

The desired valving action is provided by a valve element 160 having a stem 160a which extends through the axial port 153a and terminates at its lower end in a head 160b. The head 160b has a peripheral groove which mounts an 0-ring 161. The upper end of the stem 160a is formed integral with a finger actuator 162 having an enlarged button portion 162a overlying the proximal end 111a of the syringe 110. An 0-ring 163 is mounted in a groove in the actuator 162. The 0-ring 161 in the head of the valve element 160 is normally biased into engagement with the end wall 153 around the axial port 153a by means of a helical compression spring 165 mounted in the valve cavity 154 and engaged between the end wall 153 and a shoulder on the valve actuator 162. The 0-ring 161 on the head 160b provides the sole means for retaining the valve actuator 162 engaged with the valve body 151. As a result, after the set screw 157 is backed-off and the flow control valve assembly 150 removed from its recess, the valve assembly 150 can be disassembled first by disconnecting the 0-ring 161 from the valve head 160b and then sliding the actuator 162 axially outward. The 0-rings 163, 155 and 156 can then be removed and replaced, the actuator 162 reinstalled, and the 0-ring 161 replaced, and the valve assembly 150 reinstalled and secured in place by means of the set screw 157.

The flow control valve assembly 150 is particularly suited for use in the autoclavable syringe 10 of FIGS. 1-8, but because of its essentially two piece machined construction having replaceable 0-rings, it may also be used readily in a conventional syringe which is not normally subjected to the high temperatures associated with sterilization in an autoclave. The relatively simple structure of the flow control valve assembly 150 renders it straightforward to manufacture by high speed mass production machinery, thereby enabling significant manufacturing cost savings to be realized.

In view of the foregoing, it should be apparent that the present invention now provides an improved syringe which is particularly suited for sterilization methods known to date including autoclave. This is due to its capability of being readily disconnected from compressible gas (including air) and noncompressable liquid (including water) supply hoses, and because of other design features which both resist the high temperatures and increased chemical reaction rates at higher temperatures encountered in sterilization procedures and afford field parts replacement should such become necessary after repeated sterilization cycles. Thus, the syringe of the present invention may find widespread applicability, not only in the dental operatory, but also in the medical field where surgical procedures are performed in hospital operating rooms and nursing care delivered at bedside and where sterile fields must be maintained.

While preferred embodiments of the present invention have been described in detail, various modifications, alterations and changes may be made without departing from the spirit and scope of the present invention as defined in the appended claims.

We claim:

1. In a syringe having a flow control nozzle mounted on a proximal end of a handle and communicating through a bore in the handle with a source of fluid connected to a distal end of the handle, and flow control valve means mounted in the bore for controlling flow of the fluid to the nozzle, the improvement wherein the flow control valve means includes a tubular valve body for insertion in the bore and having an end wall with an axial port and at least one lateral port adjacent said end wall, a cavity in said valve body providing fluid communication between said ports, a valve stem mounted in said valve body cavity for axial motion relative to said axial port, said valve stem having a head extending through said axial port with an annular groove adjacent said end wall, an 0-ring removably mounted in said groove and axially movable with said head for seated engagement with said end wall around said axial port, biasing means in said cavity operatively connected between said stem and said valve body for biasing said 0-ring into said seated engagement, and finger operable means on said stem for displacing said 0-ring out of said seated engagement to afford fluid flow through said ports, said 0-ring cooperating with said end wall to provide the sole means for maintaining said stem operatively assembled with said valve body.

2. Apparatus according to claim 1 wherein said finger operable means includes a push button on said stem remote from said head, and said biasing means includes a helical spring mounted in said valve cavity and engaged between said push button and said end wall for urging said 0-ring into said seated engagement and to react against the spring bias both to seal said axial port and to releasably maintain said push button connected to said valve body.

3. Apparatus according to claim 2 including coupling means for releasably coupling the distal end portion to an end portion of a flexible hose connected to a source of fluid flowable with respect to said nozzle, said coupling means including a first coupling component mountable on said hose end portion and a second coupling component carried by said distal end portion of said handle, said first and second coupling components being telescopically matingly engageable and disengageable with one another and having cooperating valving and actuator means operable automatically upon engagement to provide fluid communication between said hose and said handle when said coupling elements are locked together and upon disengagement to block said fluid communication.

4. A valve assembly for a dental syringe comprising, in combination:
   a valve body formed to be inserted in a fluid line and having a cylindrical cavity with a side port and an axial port at one end;
   a valve stem axially movable in said cavity and including a cylindrical head at said one end extending through said axial port, said head having an annular groove adjacent the exterior side of said end;
   an 0-ring removably mounted in said groove and axially movable with said head for seated engagement with the exterior side of said end around said axial port;
   force exerting means in said cavity operatively connected between said valve stem and said valve body for urging said 0-ring into said seated engagement; and said O-ring providing the sole means for maintaining said valve stem operatively assembled in said valve body.

5. A valve assembly according to claim 4 wherein:
said valve stem further includes an actuator at the other end for manually displacing said O-ring out of said seated engagement.

* * * * *